(12) United States Patent
Gorski et al.

(10) Patent No.: US 11,492,331 B2
(45) Date of Patent: Nov. 8, 2022

(54) REDOX SUBSTRATES FOR LEUKOCYTE ESTERASE

(71) Applicant: THE BOARD OF REGENTS OF THE UNIVERSITY OF TEXAS SYSTEM, Austin, TX (US)

(72) Inventors: Waldemar Gorski, Helotes, TX (US); Stanton McHardy, Waring, TX (US); Douglas Hanson, San Antonio, TX (US); Travis Menard, San Antonio, TX (US); Andrew Fleischman, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/762,686

(22) PCT Filed: Nov. 8, 2018

(86) PCT No.: PCT/US2018/059800
§ 371 (c)(1),
(2) Date: May 8, 2020

(87) PCT Pub. No.: WO2019/094575
PCT Pub. Date: May 16, 2019

(65) Prior Publication Data
US 2021/0171467 A1    Jun. 10, 2021

Related U.S. Application Data

(60) Provisional application No. 62/583,211, filed on Nov. 8, 2017.

(51) Int. Cl.
*C07D 213/71* (2006.01)
*G01N 27/27* (2006.01)

(52) U.S. Cl.
CPC .......... *C07D 213/71* (2013.01); *G01N 27/27* (2013.01)

(58) Field of Classification Search
None
See application file for complete search history.

(56) References Cited

U.S. PATENT DOCUMENTS

| | | | |
|---|---|---|---|
| 5,464,739 A | 11/1995 | Johnson et al. | |
| 2003/0065193 A1 | 4/2003 | Thorsett et al. | |

FOREIGN PATENT DOCUMENTS

WO    WO 2017/165222    9/2017

OTHER PUBLICATIONS

Database Registry Chemical Abstracts Service, Columbus, Ohio, Accession No. RN 1277793-43-7, Entered STN: Apr. 10, 2011.*
Database Registry Chemical Abstracts Service, Columbus, Ohio, Accession No. RN 1286635-97-9, Entered STN: Apr. 27, 2011.*
Bimstein et al., "Leukocyte Esterase and Protein Levels in Saliva, as Indicators of Gingival and Periodontal Diseases in Children", *Pediatr. Dentist.*, 26: 310-315, 2004.
Colvin et al., "Leukocyte esterase analysis in the diagnosis of joint infection: Can we make a diagnosis using a simple urine dipstick?", *Skeletal Radiol*, 44: 673-677, 2015.
Ducharme et al., "Can Urine Cultures and Reagent Test Strips Be Used to Diagnose Urinary Tract Infection in Elderly Emergency Department Patients Without Focal Urinary Symptoms?", *Can. J. Emergen. Med.*, 9:87-92, 2007.
Hanson et al., "Electrochemical Substrate and Assay for Esterolytic Activity of Human White Blood Cells", *Anal. Chem.*, 89: 7781-7787, 2017.
Hanson et al., "Synthesis and Characterization of Pyridine Compounds for Amperometric Measurements of Leukocyte Esterase", *Chembiochem*, 19(14): 1488-1491, 2018.
International Search Report and Written Opinion issued in corresponding International Patent Application No. PCT/US18/59800 dated Dec. 31, 2018.
Jackson et al., "A Kinetic Study of the Hydrolysis of the N-tosylalanine Ester of 3-hydroxy-5-phenylpyrrole and Related Compounds by Human Leukocyte Elastase", *Arch. Biochem. Biophys.*, 323: 108-114, 1995.
Johnson et al., "Chromogenic Lactate-Leukocyte Esterase Substrates", *Bioconjugate Chem.*, 8: 76-80, 1997.
Kotani et al., "Development of a new point-of-care testing system for measuring white blood cell and C-reactive protein levels in whole blood samples", *Clinica Chim. Acta*, 433: 145-149, 2014.
Mastropaolo et al., "An ultraviolet spectrophotometric assay for α-naphthyl acetate and a-naphthyl butyrate esterases", *Anal. Biochem.*, 115: 188-193, 1981.
McNabb et al., "Determining False Positive Rates of Leukocyte Esterase Reagent Strip When used as a Detection Tool for Joint Infection", *J. Arthroplasty*, 32: 220-222, 2017.
Murthy et al., "A Simple Spectrophotometric Assay for Urinary Leukocyte Esterase Activity", *Biochem. Med. Metabol. Bio.*, 40: 260-268, 1988.
Schechter et al., "On the Size of the Active Site in Proteases. I. Papain", *Biochem. Biophys. Res. Commun.*, 27: 157-162, 1967.
Scheer, W.D., "The Detection of Leukocyte Esterase Activity in Urine with a New Reagent Strip", *Am. J. Clin. Pathol.*, 87: 86-93, 1987.

(Continued)

*Primary Examiner* — Samantha L Shterengarts

(57) ABSTRACT

Certain embodiments are directed hydrophilic redox substrates for leukocyte esterase (LE). In certain aspects a hydrophilic redox leukocyte esterase substrate or a small molecule enzyme substrate for use in methods and/or devices to electrochemically detect and/or measure LE activity in a sample.

10 Claims, 2 Drawing Sheets

(56) References Cited

OTHER PUBLICATIONS

Yadav et al., "Importance of Leucocyte Esterase Test in Diagnosis of Urinary Tract Infection", *Int. J. Pharm. Bio Sci.*, 6B: 370-375, 2015.

Zhang et al., "Electrochemical Coupled-Enzyme Assays at Carbon Nanotubes", *Anal. Chem.* 86: 9330-9334, 2014.

Zhang et al., "Rapid Electrochemical Enzyme Assay With Enzyme-Free Calibration", *Anal. Chem.*, 85: 6026-6032, 2013.

* cited by examiner

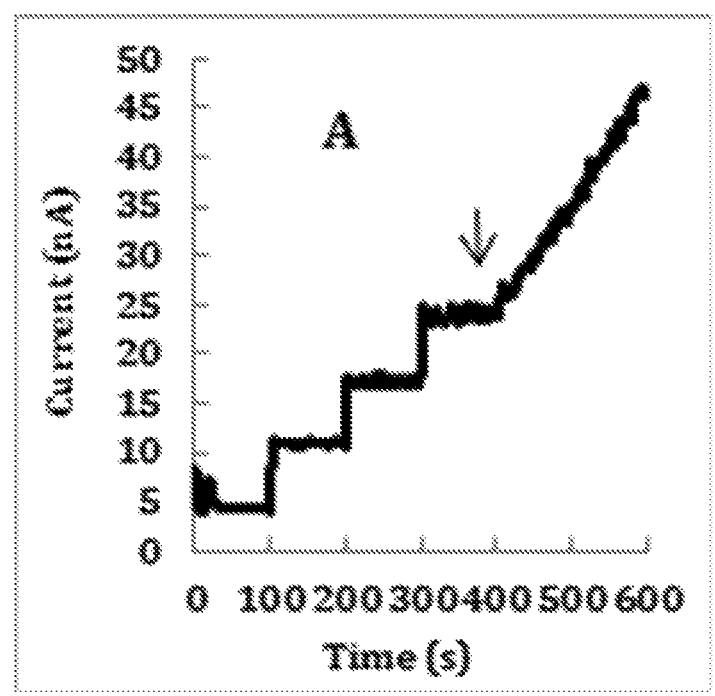
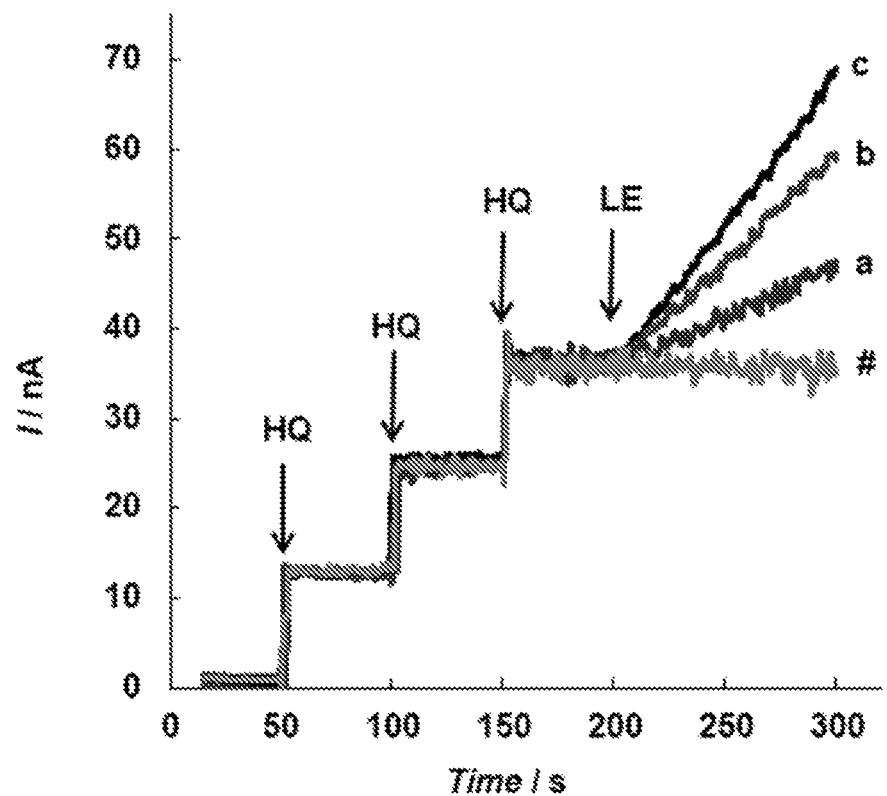
FIGS. 1A-B

REDOX SUBSTRATES FOR LEUKOCYTE ESTERASE

CROSS REFERENCE TO RELATED APPLICATIONS

This Application is a national phase under 35 U.S.C. § 371 of International Application No. PCT/US2018/059800, filed Nov. 8, 2018, which claims priority to U.S. Provisional Patent Application Ser. No. 62/583,211 filed Nov. 8, 2017, the entire contents of each of which are incorporated herein by reference in their entirety.

STATEMENT REGARDING FEDERALLY FUNDED RESEARCH

None

BACKGROUND OF THE INVENTION

A. Field of the Invention

The invention generally concerns compositions, devices, kits, and methods for detecting the presence of leukocyte esterase. In particular aspects the invention concerns esters hydrolyzable by leukocyte esterase and devices and kits including or using the same.

B. Description of Related Art

The activity of enzyme leukocyte esterase (LE) has been commonly used as a proxy for the presence of white blood cells associated with infection. It has been assessed solely by colorimetry, which is quite limiting. Colorimetry cannot be effectively used in turbid or color samples, e.g., bloody biological fluids, and it often requires toxic chromogenic agents, multiple liquid-handling steps, and time-consuming incubation.

The enzyme leukocyte esterase (LE) is an important biomarker for diagnosing and monitoring infections, a common and often devastating clinical problem. However, the development of novel LE assays has been limited (Kotani et al., *Clinica Chim. Acta*, 2014, 433:145-49; Murthy and Karmen, *Biochem. Med. Metabol. Bio.*, 1988, 40:260-68; Mastropaolo and Yourno, *Anal. Biochem.* 1981, 115:188-93; Johnson and Schaeper, *Bioconjugate Chem.* 1997, 8: 76-80) and the relevant literature is dominated by the studies of clinical utility of existing LE kits and strips (McNabb et al., *J. Arthroplasty* 2017, 32:220-22; Colving et al., *Skeletal Radiol.* 2015, 44:673-77; Yadav et al., *Int. J. Pharm. Bio. Sci.* 2015, 6B:370-75; Ducharme et al., *Can. J. Emergen. Med.* 2007, 9:87-92; Bimstein et al., *Pediatr. Dentist.* 2004, 26:310-15), which are all based on optical assays. While such assays have been fairly useful, they often provide only semi-quantitative readings and have a limited resolution (especially, in color or opaque media).

Examples of commercially-available leukocyte esterase reagent strips are CHEMSTRIP® 9 and CHEMSTRIP® LN (both sold by Bio-Dynamics, Indianapolis, Ind.); and MULTISTIX® 2 Reagent Strips and AMES LEUKOSTIX® (both available from Ames, Division of Miles Laboratory, Elkhart, Ind.). Techniques for using these commercially-available leukocyte esterase reagent strips are well known from their use for in vitro urine analysis (e.g., Scheer, *Am. J. Clin. Pathol.*, 1987, 87:86-93).

All of these commercially-available leukocyte esterase reagent strips contain an indoxyl carbonic acid ester which is hydrolyzed to indoxyl by leukocyte esterase. The indoxyl thus formed reacts with a diazonium compound in the strip to produce a color which indicates the presence of the leukocyte esterase. The degree of darkening of the strips is a semi-quantitative indication of the amount of leukocyte esterase present in a sample.

SUMMARY OF THE INVENTION

Compounds, compositions, and devices of the current invention provide a solution to the problems associated with current colorimetric LE assays. In particular, the esterase substrates described herein provide for electrochemical detection. By way of example, the inventors have synthesized particular LE substrates to detect LE activity in a more sensitive and quantitative manner, which results in LE assays based on the described substrates having appropriate electrochemical characteristics that enhance LE detection. Electrochemistry can be used to quantify LE activity with high resolution using the ester compounds described herein. Enzyme-free calibration, selectivity, sensitivity, and short analysis time are some of the benefits gained using assays described herein.

A class of substrates is described herein that enable electrochemical LE assays that overcome the limits of optical assays and open the prospect of point-of-care devices for the rapid quantification of infection. In particular, the inventors describe the synthesis of hydrophilic redox substrates for LE, their enzymatic kinetics, and their performance in the development of electrochemical LE assays.

Certain embodiments are directed hydrophilic redox substrates for LE. In certain aspects a hydrophilic redox leukocyte esterase substrate or a small molecule enzyme substrate having a chemical formula of Formula I or a pharmaceutically acceptable salt thereof:

Formula I

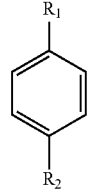

wherein, $R_1$ has the general structure

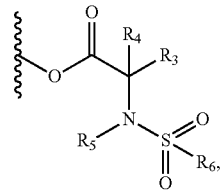

where $R_3$ and $R_4$ are independently hydrogen, $C_1$ to $C_8$ alkyl, substituted $C_1$ to $C_8$ alkyl, $C_3$ to $C_7$ cycloalkyl, or substituted $C_3$ to $C_7$ cycloalkyl; $R_5$ is independently hydrogen, saturated $C_1$-$C_6$ alkyl, mono-unsaturated $C_1$-$C_6$ alkyl, poly-unsaturated $C_1$-$C_6$ alkyl, $C_3$ to $C_7$ cycloalkyl, or substituted $C_3$ to $C_7$ cycloalkyl; and $R_6$ is heterocycle or heteroaryl, wherein said heterocycle or heteroaryl is optionally substituted with 1 to 3 halogens, $C_1$ to $C_3$ alkyl, OH, $NH_2$, $C(O)NH_2$, $CO_2H$, $CH_2OH$ and —$C(O)NHR'$, $C(O)NR'_2$, $OR'$, $CO_2R'$, $CH_2OR'$, $NHR'$, $N(R')_2$, or combinations thereof, where in R' is $C_1$ to $C_3$ alkyl or halogenated alkyl; and R2 is (a) the same as R1, or (b) $R_2$ is O—$R_7$, wherein $R_7$ is saturated $C_1$-$C_6$ alkyl, mono-unsaturated $C_1$-$C_6$ alkyl, poly-unsaturated $C_1$-$C_6$, or cycloalkyl, where in the cycloakyl can be optionally substituted with 1 to 3 halogens, $C_1$ to $C_3$ alkyl, OH, $NH_2$, $C(O)NH_2$, $CO_2H$, $CH_2OH$, $C(O)NHR''$, $C(O)NR''_2$, $OR''$ $CH_2OR''$, $NHR''$, —$N(R'')_2$ or combinations thereof, where R" is $C_1$ to $C_3$ alkyl or halogenated alkyl.

In certain aspects the heterocycle or heteroaryl is pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, or azaindolyl.

In a further aspect the heterocycle is aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, or 1,4-dioxaspiro[4.2]heptyl.

In a particular aspect the substrate is 4-{[(2S)-2-(4-methylbenzenesulfonamido)propanoyl]oxy}phenyl(2S)-2-(4-methylbenzenesulfonamido)propanoate; 4-{[(2S)-2-(pyridine-3-sulfonamido)propanoyl]oxy}phenyl (2S)-2-(pyridine-3-sulfonamido)propanoate; 4-{[(2S)-2-(6-methoxypyridine-3-sulfonamido)propanoyl]oxy}phenyl (2S)-2-(6-methoxypyridine-3-sulfonamido)propanoate; or methyl 5-{[(2S)-1-(4-{[(2S)-2-[5-(methoxycarbonyl)pyridine-3-sulfonamido]propanoyl]oxy}phenoxy)-1-oxopropan-2-yl]sulfamoyl}pyridine-3-carboxylate.

Certain embodiments are directed to methods for detecting leukocyte esterase (LE) activity by contacting a sample with a hydrophilic redox substrate described herein forming a test sample and detecting cleavage of the substrate by LE in the test sample. In certain aspects detecting cleavage of the substrate by LE in the test sample is by electrochemical detection. In certain aspects the substrate concentration in the test sample is between 1.0, 10, 50, 100, 500, 750 and 1000, 1250, 1500, 1750, 2000 mg/L, including all values and ranges there between.

Certain embodiments are directed to a reaction medium comprising a hydrophilic redox substrate described herein in contact with an electrode. In certain aspects the electrode is a carbon electrode, a glassy carbon electrode, a noble metal (e.g., Pt or Au) electrode.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

"Measuring leukocyte esterase", as used herein, is detecting the presence of leukocyte esterase; or quantitatively or semi-quantitatively measuring the amount or concentration of leukocyte esterase in a sample. Systems, kits, device, and/or reagents that can be used for measuring leukocyte esterase are described more fully herein.

As used herein, the term "$IC_{50}$" refers to an inhibitory dose that results in 50% of the maximum response obtained.

The term "effective," as that term is used in the specification and/or claims, means adequate to accomplish a desired, expected, or intended result.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIGS. 1A-B. (A) ICECEA I-t trace recorded at 0.40 V in a stirred pH 7.40 assay solution containing a tested compound. Each current step is due to the addition of hydroquinone calibrating aliquot to a solution. The arrow shows the addition of LE. The ascending I-t segment after arrow indicates that a compound was recognized by LE as its substrate. Otherwise, this segment was flat. (B) ICECEA current-time (I-t) traces recorded at a GC electrode in a stirred assay solution of compound (a) I, (b) II, (c) III. Trace # is for a precursor 1 to compounds I-III (Scheme 2). Arrows indicate the addition of 50 µL aliquots of hydroquinone (HQ) and leukocyte esterase (LE) to generate 0.54 µM HQ and 86.7 µg L$^{-1}$ LE protein in a solution. Assay solution, pH 7.40 PBS solution containing 60 µg mL$^{-1}$ of compound I-III or precursor 1. Traces were overlaid and shortened to show only the linear portion of ascending I-t segments. Potential, 0.40 V.

DETAILED DESCRIPTION OF THE INVENTION

Figure 2:
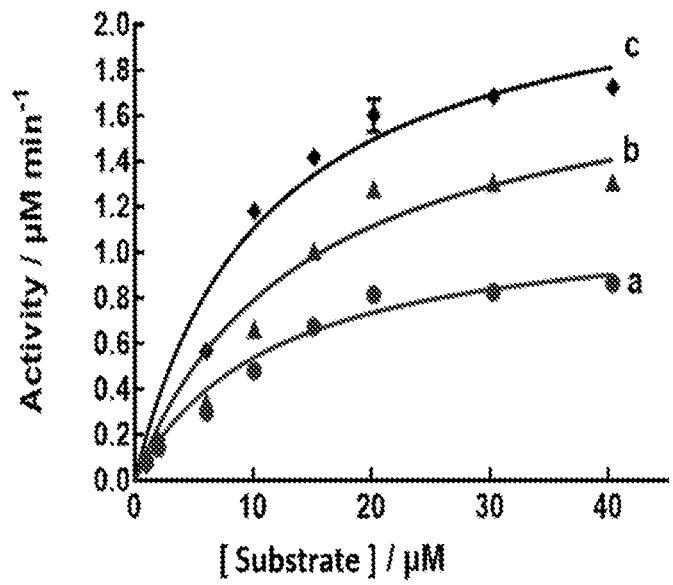
FIG. 2. Michaelis-Menten plots for 6.0 nM LE and 1-40 µM compound: (a) I, (b) II, and (c) III, in PBS (pH 7.40). The solid lines represent the best fit to the experimental points based on the nonlinear regression.

Embodiments of the present invention include compounds, devices, and/or diagnostic methods for detecting or evaluating the presence of infection or inflammation in humans or animals. These methods can include measuring the amount of leukocyte esterase (LE) present in sample obtained from the human or animal being tested or diagnosed.

A. Hydrophilic Ester Based Compounds

Certain embodiments are directed to 1,4-hydroquinone ester based compounds as small molecule enzyme substrates. In certain aspects the small molecule enzyme substrates can be utilized in an electrochemical assay of enzymatic activity of leukocyte esterase (LE) for the rapid and accurate diagnosis of the presence and extent of infection in human and animal samples.

Certain embodiments are directed toward a compound of Formula I or a pharmaceutically acceptable salt thereof:

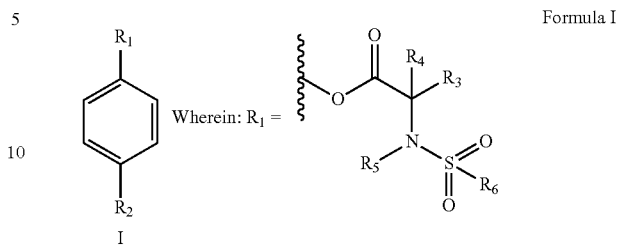

Formula I

Wherein, $R_1$ is the general structure for $R_1$ as shown above. In certain aspects $R_1$ can be equal to $R_2$. In a further aspect $R_1$ is not equal to $R_2$, in which case, $R_2$ can be O—$R_7$, wherein $R_7$ is $C_1$-$C_6$ saturated or mono- or poly-unsaturated alkyl or cycloalkyl, which can be independently substituted with 1-3 halogens, alkyl ($C_1$ to $C_3$), —OH, —$NH_2$, —C(O)$NH_2$, —$CO_2$H, —$CH_2$OH, —C(O)NHR, —C(O)$NR_2$, —OR—$CH_2$OR, —NHR, —N(R)$_2$ or combinations thereof, where in R in the substituents is alkyl ($C_1$ to $C_3$) or halogenated alkyl (i.e., $CF_3$) optionally substituted with 1-3 halogens, alkyl ($C_1$ to $C_3$), cycloalkyl ($C_3$-$C_7$), heterocyclic, aryl and heteroaryl, wherein said heterocyclic, aryl and heteroaryl.

In certain aspects, $R_3$ and $R_4$ are independently hydrogen or alkyl ($C_1$ to $C_8$) and substituted alkyl, cycloalkyl ($C_3$ to $C_7$) and substituted cycloalkyl. $R_3$ and $R_4$ to which the carbon atom they are attached can exist in either the (R)- or (S)-chiral or enantiomeric forms. $R_5$ is independently hydrogen or $C_1$-$C_6$ saturated or mono- or poly-unsaturated alkyl or cycloalkyl. $R_6$ is heterocyclic and heteroaryl, wherein said heterocyclic and heteroaryl is optionally substituted with 1-3 halogens, alkyl ($C_1$ to $C_3$), —OH, —$NH_2$, —C(O)$NH_2$, —$CO_2$H, —$CH_2$OH and —C(O)NHR, —C(O)NR'$_2$, —OR', $CO_2$R', —$CH_2$OR, —NHR' or —N(R')$_2$ or combinations thereof, where in R is alkyl ($C_1$ to $C_3$) or halogenated alkyl (e.g., $CF_3$).

In certain aspects heterocyclic and heteroaryl groups can be pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, or azaindolyl.

In other aspects non-aromatic heterocyclic groups can be aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, or 1,4-dioxaspiro[4.2]heptyl.

The compounds of the Formula I may be prepared by the methods described below, together with synthetic methods known in the art of organic chemistry, or modifications and derivatizations that are familiar to those of ordinary skill in the art.

Preferred methods include, but are not limited to, those described below. During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; and T. W. Greene and P. G. M. Wuts, Protective Groups in Organic Chemistry, John Wiley & Sons, 1991, which are hereby incorporated by reference.

Compounds of Formula I or their pharmaceutically acceptable salts, can be prepared according to reaction Scheme 1 below. Isolation and purification of the products is accomplished by standard procedures, which are known to a chemist of ordinary skill. The following schemes and examples provide examples of the processes for making compounds of Formula I. It is to be understood, however, that the invention, as fully described herein and as recited in the claims, is not intended to be limited by the details of the following examples. Unless otherwise noted, $R_1$ through $R_6$ are defined as above.

Referring to scheme 1, treatment of an appropriately substituted hydroquinone of compound 1 with an appropriately substituted N-protected amino acid, such as (tert-butoxycarbonyl)-L-alanine, in the presence of a suitable coupling reagent such as EDCI, a base such as TEA in $CH_3CN$, at temperatures ranging from 20° C. to 150° C., including all values and ranges there between, produces the desired ester compound 2. Alternative conditions for this transformation also include the use of various coupling reagents, such as DCC, HATU, and the like, in the presence of suitable bases such as DIEA, TEA and the like and solvents such as ACN, DMF, THF and the like. Treatment of compound 2 with a suitable acid such as HCl, TFA and the like will produce the desired free amine 3. Coupling of amine 3 and an appropriately substituted sulfonyl chloride ($R_6$—$SO_2Cl$) in the presence of a suitable base (TEA, DMAP, pyridine and the like), produces the desired product compound 4.

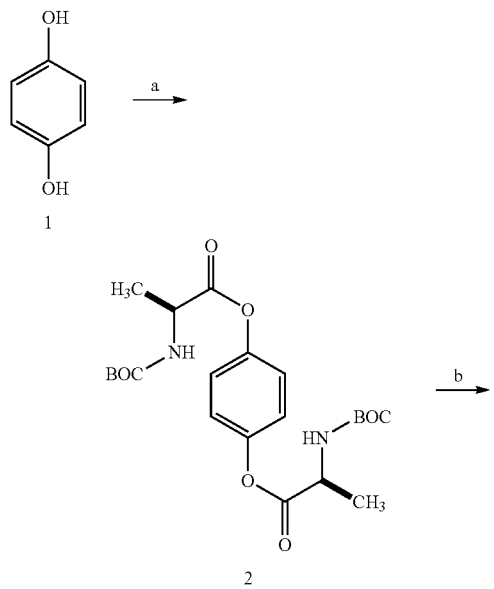

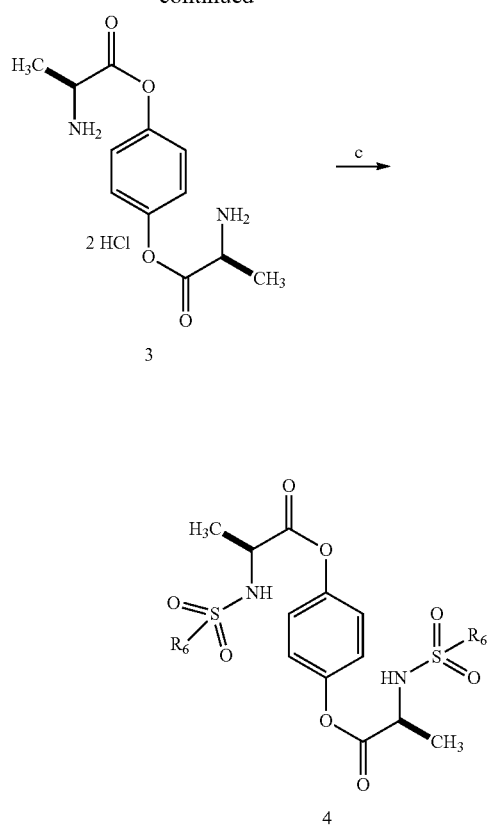

Reagents and Conditions: a) (tert-butoxycarbonyl)-L-alanine, EDCI, TEA, ACN, R.T.; b) 4N HCl, Dioxane, R.T.,; c) $R_6$—$SO_2Cl$, 4-DMAP, TEA, DCM.

Alternatively, compounds of Formula I, or their pharmaceutically acceptable salts can be prepared according to reaction Scheme 2 below, wherein $R_1$ is not equal to $R_2$, in which case, $R_2$ can be O—$R_7$ as defined above.

Referring to scheme 2, treatment of an appropriately substituted hydroquinone compound 1 with an appropriately substituted alkylating agent ($R_7$—Br), in the presence of a base such as NaH in THF, at temperatures ranging from 20° C. to 150° C., including all values and ranges there between, produces ether compound 5. Alternative conditions for this transformation also include the use of various bases and solvents such as $K_2CO_3$, $Cs_2CO_3$, $Na_2CO_3$, LDA, K-tOBu and the like and polar aprotic solvents such as DMSO, DMF and the like. Treatment of ether compound 5 with an appropriately substituted N-protected amino acid, such as (tert-butoxycarbonyl)-L-alanine, in the presence of a suitable coupling reagent such as EDCI, a base such as TEA in $CH_3CN$, at temperatures ranging from 20° C. to 150° C., including all values and ranges there between, produces ester compound 6. Alternative conditions for this transformation also include the use of various coupling reagents, such as DCC, HATU, and the like, in the presence of suitable bases such as DIEA, TEA and the like and solvents such as ACN, DMF, THE and the like. Treatment of compound 6 with a suitable acid such as HCl, TFA and the like produces free amine 7. Coupling of the amine 7 and an appropriately substituted sulfonyl chloride ($R_6$—$SO_2Cl$) in the presence of a suitable base (TEA, DMAP, pyridine and the like), produces product compound 8.

SCHEME 2. Alternative synthesis of compounds of Formula I

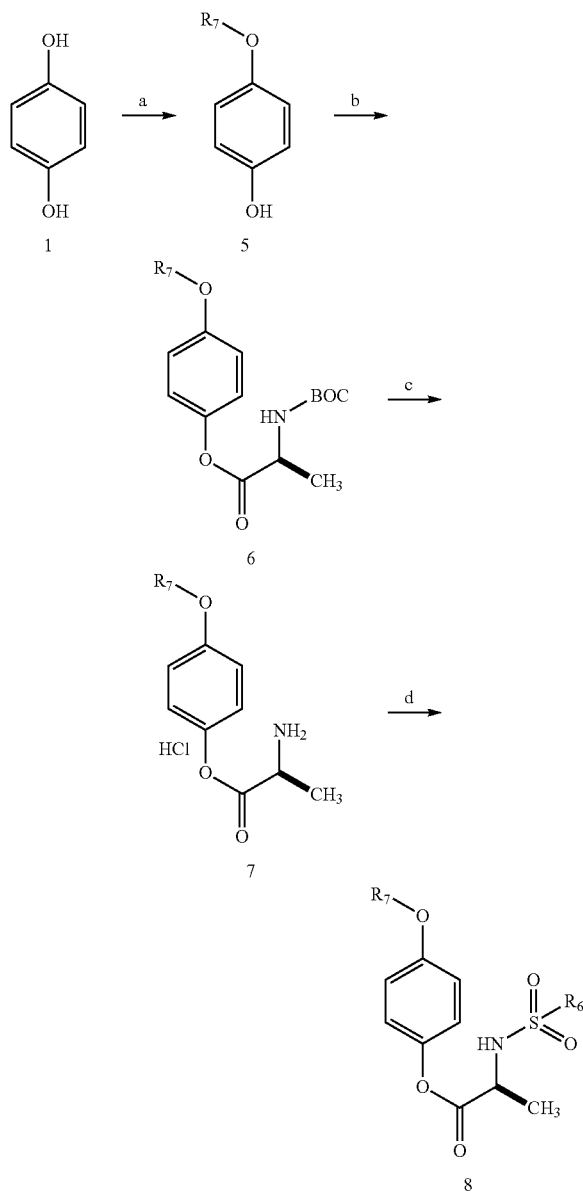

Reagents and Conditions: a) R₇—Br, K₂CO₃; b) (tert-butoxycarbonyl)-L-alanine, EDCl, TEA, ACN, R.T.; c) 4 N HCl, Dioxane, R.T.; d) R₆—SO₂Cl, 4-DMAP, TEA, DCM.

Finally, pharmaceutically acceptable salts of compounds of Formula I may be prepared by one or more of three methods: (i) by reacting the compound of Formula I with the desired acid; (ii) by removing an acid-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

Pharmaceutically acceptable salts of the compounds of Formula I include the acid or base addition salts thereof. All three reactions are typically carried out in solution. The resulting salt may precipitate out and be collected by filtration or may be recovered by evaporation of the solvent. The degree of ionization in the resulting salt may vary from completely ionized to almost non-ionized. Suitable non-toxic, acid-addition pharmaceutically acceptable salts include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable non-toxic, base-addition pharmaceutically acceptable salts include, but are not limited to aluminium, arginine, benzathine, calcium, choline, diethylamine, diolamine, glycine, lysine, magnesium, meglumine, olamine, potassium, sodium, tromethamine and zinc salts. For a review on suitable salts, see Handbook of Pharmaceutical Salts: Properties, Selection, and Use by Stahl and Wermuth (Wiley-VCH, 2002).

Included within the scope of the present invention are all stereoisomers, geometric isomers and tautomeric forms of the compounds of Formula I, including compounds exhibiting more than one type of isomerism, and mixtures of one or more thereof.

The present invention can include all pharmaceutically acceptable isotopically-labelled compounds of Formula I wherein one or more atoms are replaced by atoms having the same atomic number, but an atomic mass or mass number different from the atomic mass or mass number which predominates in nature.

Synthesis of 1,4-phenylene (2S,2'S)-bis(2-((tert-butoxycarbonyl)amino)propanoate). A flame-dried vessel purged with nitrogen was charged with Hydroquinone (1.04 g, 9.5 mmol) and acetonitrile (120 mL) at room temperature. To this stirring solution was added (tert-butoxycarbonyl)-L-alanine (3.62 g, 19 mmol) and 4-dimethylaminopyridine (0.117 g, 0.96 mmol). The mixture was allowed to stir for 5 minutes before adding N-(3-Dimethylaminopropyl)-N'-ethylcarbodiimide hydrochloride (3.9 g, 20 mmol), followed by triethylamine (2.8 mL, 20 mmol). The reaction mixture was stirred at room temperature for 12 hours. The mixture was poured into ice-cold 1N HCl (300 mL) and allowed to stir for 30 minutes. The resulting precipitate was filtered and dried under reduced pressure. The crude solid was recrystallized in a mixture of hexanes and ethyl acetate (4:1). The solid was filtered and dried under reduced pressure to yield 2.57 g (64% yield) of 1,4-phenylene (2S,2'S)-bis(2-((tert-butoxycarbonyl)amino)propanoate) as a white solid; 1H NMR (400 MHz, CDCl3) δ 7.12 (s, 4H), 5.07 (br s, 2H), 4.52 (br m, 2H), 1.51 (d, J=7.7 Hz, 6H), 1.47 (s, 18H).

Synthesis of 1,4-phenylene (2S,2'S)-bis(2-aminopropanoate)-bis hydrochloride. A 4 M HCl solution in 1,4-dioxane (60 mL) was slowly added to 1,4-phenylene (2,2'S)-bis(2-((tert-butoxycarbonyl)amino)propanoate) (1.87 g, 4.4 mmol) at room temperature. The mixture was allowed to stir for 30 minutes at room temperature, after which time the resulting precipitate was filtered, washed with cold diethyl ether and dried under reduced pressure. The resulting white solid, 1,4-phenylene (2,2'S)-bis(2-aminopropanoate)-bis hydrochloride (1.31 g, 93% yield) was used without further purification; 1H NMR (400 MHz, CD3OD) δ 7.30 (s, 4H), 4.42 (q, J=7.2 Hz, 2H), 1.72 (d, J=7.3 Hz, 6H). MS (m/z) 505.3 (2M+H+), 253.2 (M+H+).

Synthesis of 4-((tosyl-L-alanyl)oxy)phenyl tosyl-L-alaninate. To a stirring solution of 1,4-phenylene (2S,2'S)-bis(2-aminopropanoate)-bis hydrochloride (0.222 g, 0.7 mmol) in anhydrous dichloromethane (3.5 mL) under an $N_2$ gas atmosphere was added 4-toluenesulfonyl chloride (0.394 g, 2.1 mmol), 4-dimethylaminopyridine (0.0087 g, 0.07 mmol), and triethylamine (0.40 mL, 2.9 mmol). The mixture was allowed to stir at room temperature for 4 hours. The crude reaction mixture was treated with equal portions (~5 mL) of water and ethyl acetate and transferred to a separatory funnel. The layers were separated and the aqueous layer was extracted with ethyl acetate (3×2 mL). The combined organic layers were dried with anhydrous sodium sulfate, decanted, and concentrated under reduced pressure. The crude product was dissolved in dichloromethane and precipitated out with hexanes. The solid was filtered, washed with hexanes, and dried under reduced pressure to yield 4-((tosyl-L-alanyl)oxy)phenyl tosyl-L-alaninate (0.255 g, 70% yield) as a white solid; 1H NMR (400 MHz, DMSO) δ 8.47 (d, J=7.6 Hz, 2H), 7.72 (d, J=8.1 Hz, 4H), 7.39 (d, J=8.2 Hz, 4H), 6.92 (s, 4H), 4.14-4.05 (m, 2H), 2.37 (s, 6H), 1.33 (d, J=7.1 Hz, 6H), 13C NMR (101 MHz, CDCl3) δ 170.89, 147.79, 144.02, 136.87, 129.94, 127.42, 122.02, 51.72, 21.65, 19.69. MS (m/z) 559.0 (M+H+)

TABLE 1

Representative compounds.

| Molecule Name | Structure | IUPAC NAME |
|---|---|---|
| CIDD-0072492 | (structure shown) | 4-{[(2S)-2-(4-methylbenzenesulfonamido)propanoyl]oxy}phenyl(2S)-2-(4-methylbenzenesulfonamido)propanoate |
| CIDD-0072852 | (structure shown) | 4-{[(2S)-2-(pyridine-3-sulfonamido)propanoyl]oxy}phenyl (2S)-2-(pyridine-3-sulfonamido)propanoate |

TABLE 1-continued

Representative compounds.

| Molecule Name | Structure | IUPAC NAME |
|---|---|---|
| CIDD-0072853 | 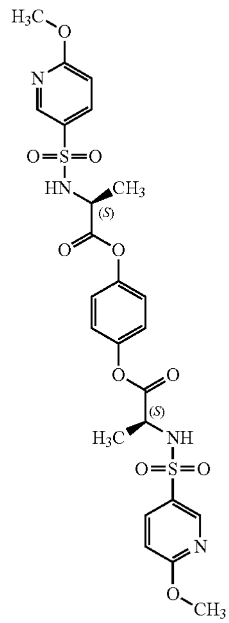 | 4-{[(2S)-2-(6-methoxypyridine-3-sulfonamido)propanoyl]oxy} phenyl (2S)-2-(6-methoxypyridine-3-sulfonamido) propanoate |
| CIDD-0072899 | 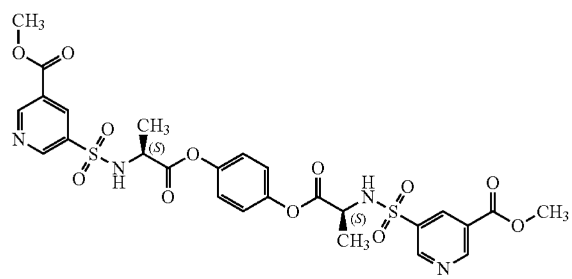 | methyl 5-{[(2S)-1-(4-{[(2S)-2-[5-(methoxycarbonyl)pyridine-3-sulfonamido]propanoyl]oxy}phenoxy)-1-oxopropan-2-yl]sulfamoyl}pyridine-3-carboxylate |

B. Chemical Definitions

Various chemical definitions related to such compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer.

As used herein, the term "water soluble" or "hydrophilic" means that the compound dissolves in water. In the context of a LE assay, "water soluble" is the minimum concentration of LE substrate that generates a measurable amount of current from the LE+substrate reaction, which can be as low as 1 micromole/liter.

As used herein, the term "nitro" means —$NO_2$; the term "halo" or "halogenated" designates —F, —Cl, —Br or —I; the term "mercapto" means —SH; the term "cyano" means —CN; the term "azido" means —$N_3$; the term "silyl" means —$SiH_3$, and the term "hydroxyl" means —OH.

The term "alkyl," by itself or as part of another substituent, means, unless otherwise stated, a linear (i.e. unbranched) or branched carbon chain, which may be fully saturated, mono- or polyunsaturated. An unsaturated alkyl group is one having one or more double bonds or triple bonds. Saturated alkyl groups include those having one or more carbon-carbon double bonds (alkenyl) and those having one or more carbon-carbon triple bonds (alkynyl). The groups, —$CH_3$ (Me), —$CH_2CH_3$(Et), —$CH_2CH_2CH_3$(n-Pr), —$CH(CH_3)_2$ (iso-Pr), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term "halogenated alkyl" means a straight-chain or branched saturated monovalent hydrocarbon group of one to twelve carbon atoms, wherein at least one of the carbon atoms is replaced by a halogen atom (e.g. fluoromethyl, 1-bromo-ethyl, 2-chloro-pentyl, 6-iodo-hexyl, and the like).

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH$_2$F, —CH$_2$Cl, —CH$_2$Br, —CH$_2$OH, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, CH$_2$CH$_2$OC(O)CH$_3$, —CH$_2$CH$_2$NHCO$_2$C(CH$_3$)$_3$, and —CH$_2$Si(CH$_3$)$_3$.

The terms "cycloalkyl" and "heterocycle," by themselves or in combination with other terms, means cyclic versions of "alkyl" and "heteroalkyl", respectively. Additionally, for heterocycle, a heteroatom can occupy the position at which the heterocycle is attached to the remainder of the molecule.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)$_2$amino, alkylsulfinyl, alkylsulfonyl, arylsulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), —SO$_2$(C$_{1-4}$alkyl), —CO$_2$(C$_{1-4}$alkyl), and —O(C$_{1-4}$alkyl). In certain aspects a heterocycle or a heteroaryl is optionally substituted with 1 to 3 halogens, C$_1$ to C$_3$ alkyl, OH, NH$_2$, C(O)NH$_2$, CO$_2$H, CH$_2$OH and —C(O)NHR', C(O)NR'$_2$, OR', CH$_2$R', NHR' or N(R')$_2$, where in R' is C$_1$ to C$_3$ alkyl or halogenated alkyl. In other aspects a cycloakyl can be optionally substituted with 1 to 3 halogens, C$_1$ to C$_3$ alkyl, OH, NH$_2$, C(O)NH$_2$, CO$_2$H, CH$_2$OH, C(O)NHR", C(O)NR"$_2$, OR"CH$_2$OR", NHR", —N(R")$_2$ or combinations thereof, where R" is C$_1$ to C$_3$ alkyl or halogenated alkyl.

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means an oxygen that is double bonded to a carbon atom.

The term "alkylsulfonyl" as used herein means a moiety having the formula —S(O$_2$)—R', where R' is an alkyl group. R' may have a specified number of carbons (e.g. "C$_{1-4}$ alkylsulfonyl").

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

C. Leukocyte Esterase Assay

The compounds described herein were assessed as substrates for LE via enzyme assays based on the LE-triggered release of hydroquinone ($C_6H_6O_2$), reaction (1)

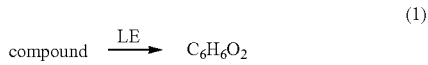
(1)

which was monitored at a glassy carbon (GC) electrode held at a potential of 0.40 V that was sufficient for the heterogeneous oxidation of $C_6H_6O_2$, reaction (2). In certain aspects the electrode can incorporate electron-conductive allotropes of carbon in place or in addition to glassy carbon including, but not limited to carbon nanotubes, graphite, graphene, boron-doped diamond etc. Also, noble metals such as platinum and gold can be used as electrodes as well.

(2)

In certain aspects, measurements were done at a constant concentration of compound by using the internally calibrated electrochemical continuous enzyme assay (ICECEA). The effectiveness of compounds as LE substrates was determined as the initial rate of reaction (1) with the help of three solutions: (A) a pH 7.40 phosphate buffer assay solution containing a substrate, (B) a pH 7.40 calibration stock solution of hydroquinone, and (C) a pH 7.40 suspension of sonicated human leukocytes. In a typical experiment, three 20-100 µL aliquots of a solution B and one 5.0-100 µL aliquot of solution C were sequentially added to the 5.00 mL of stirred assay solution A. The assays were performed in the linear range of calibration plot for hydroquinone.

FIG. 1A shows a typical ICECEA trace with three current-time (I-t) steps serving as the internal calibration and the ascending I-t segment representing the assay phase. The I-t steps are due to the oxidation of added hydroquinone (equation 2) and the ascending I-t segment is due to the oxidation of hydroquinone that was enzymatically released from a test substrate by LE (equation 1). The height of I-t steps and the angle of ascending I-t segment yield the calibration slope CS and assay slope AS, respectively, which are used in equation (3) to calculate the activity units (U) of LE. High value of U indicates a high effectiveness of a compound as a LE substrate.

$$UL^{-1} (\mu M\ min^{-1}) = \frac{AS\ (\mu As^{-1})*60(s\ min^{-1})}{CS\ (\mu A\ \mu M^{-1})} \quad (3)$$

Compound described herein can be incorporated into diagnostic products or kits. Diagnostic products that can be used for detecting LE can include at least one compound or agent useful in detecting the presence of leukocyte esterase. The term "compound or agent useful in detecting the presence of leukocyte esterase", as used herein, refers to a compound, composition, or combination thereof that is changed by the action of leukocyte esterase such that the presence of leukocyte esterase can be detected as a result of LE enzymatic activity. Compounds or agents useful for detecting the presence of leukocyte esterase are esters hydrolyzable by leukocyte esterase.

Diagnostic kits can be useful for detecting LE activity. In certain aspects kits can include an device or apparatus for collecting a sample from a human or animal being tested or diagnosed, and assay or assay device for measuring the amount of leukocyte esterase present in the sample collected.

The phrase "means for collecting a sample of fluid", as used herein, means any device or apparatus or product which is useful for removing a sample of fluid, tissue, or cells from a juman or animal being tested or diagnosed without adversely affecting the ability to detect the presence of leukocyte esterase activity in the sample. Non-limiting examples of such devices include swabs, pipettes, syringes, absorbent tapes, absorbent gauzes, absorbent strips, scoops, suction bulbs, and aspirators. A kit can include one or more diagnostic products described herein.

In certain aspects the kits can be manufactured such that the sample collecting device and the assay device are separate components in the kits. The kit can include optional components to be used with the kits (e.g., test tubes for diluting samples in; bottles containing dilution fluid for diluting samples; instruction sheets; etc.) that can be combined into one package. An example of such a package is a box which is shrink wrapped with plastic.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Redox Substrates for Enzyme Leukocyte Esterase (LE)

General procedures. All operations were carried out at room or ambient temperature, that is, in the range of 18-25° C.; evaporation of solvent was carried out using a rotary evaporator under reduced pressure with a bath of up to 50° C.; reactions were monitored by thin layer chromatography (tlc) and reaction times are given for illustration only. Unless otherwise indicated all reactions were conducted in standard commercially available glassware using standard synthetic chemistry methods and setup. All air- and moisture-sensitive reactions were performed under nitrogen atmosphere with dried solvents and glassware under anhydrous conditions. Starting materials and reagents were commercial compounds of the highest purity available and were used without purification. Solvents used for reactions were commercial dry or extra-dry or analytical grade reagents. Analytical thin layer chromatography was performed on aluminum plates coated with Merck Kieselgel 60F254 and visualized by UV irradiation (254 nm) or by staining with a solution of potassium permanganate. Flash column chromatography was performed on Biotage Isolera One 2.2 using commercial columns that were pre-packed with Merck Kieselgel 60 (230-400 mesh) silica gel. Final compounds for biological testing are all ≥95% purity as determined by HPLC-MS and 1H NMR. 1H NMR experiments were recorded on Agilent DD2 400 MHz spectrometers at ambient temperature. Samples were dissolved and prepared in deuterated solvents ($CDCl_3$, $CD_3OD$ and DMSO-d6) with residual solvents being used as the internal standard in all cases. All deuterated solvent peaks were corrected to the standard chemical shifts (CDCl3, dH=7.26 ppm; $CD_3OD$, dH=3.31 ppm; DMSO-d6, dH=2.50 ppm). Spectra were all manually integrated after automatic baseline correction. Chemical shifts (d) are given in parts per million (ppm), and coupling constants (J) are given in Hertz (Hz). The proton spectra are reported as follows: d (multiplicity, coupling constant J, number of protons). The following abbreviations were used to explain the multiplicities: app=apparent, b=broad, d=doublet, dd=doublet of doublets, ddd=doublet of doublet of doublets, dddd=doublet of doublet of doublet of doublets, m=multiplet, s=singlet, t=triplet. All samples were analyzed on Agilent 1290 series HPLC system comprised of binary pumps, degasser and UV detector, equipped with an autosampler that is coupled with Agilent 6150 mass spectrometer. Purity was determined via UV detection with a bandwidth of 170 nm in the range from 230-400 nm. The general LC parameters were as follows: Column—Zorbax Eclipse Plus C18, size 2.1×50 mm; Solvent A: 0.10% formic acid in water, Solvent B: 0.00% formic acid in acetonitrile; Flow rate—0.7 mL/min; Gradient: 5% B to 95% B in 5 min and hold at 95% B for 2 min; UV detector—channel 1=254 nm, channel 2=254 nm. Mass detector Agilent Jet Stream-Electron Ionization (AJS-ES).

The following abbreviations are used in this description: THF—tetrahydrofuran; DCM or $CH_2Cl_2$—dichloromethane; $NaHCO_3$—sodium bicarbonate; HCl—hydrogen chloride; $MgSO_4$—magnesium sulfate; $Na_2SO_4$—sodium sulfate; DME—dimethoxyethane; n-BuLi—n-butyllithium; DMF—dimethylformamide; DMSO—dimethylsulfoxide; $Et_2O$—diethyl ether; MeOH—methanol; EtOAc—ethyl acetate This non-limiting example describes redox substrates for enzyme leukocyte esterase (LE), which until recently had only chromogenic substrates. The substrates yield an electrical signal proportional to LE activity offering the prospect of infection assays not disturbed by the optical properties of solution. The kinetic constants $K_m$ and $k_{cat}$ for LE reactions with redox substrates, compounds I-III, were determined by amperometry at a carbon electrode. The specificity constant $k_{cat}/K_m$ was equal to 2.6, 3.7, and $6.1 \times 10^5$ $M^{-1}$ $s^{-1}$ for substrates containing the pyridine (I), methoxy-pyridine (II), and (methoxy-carbonyl)-pyridine (III), respectively, showing rise in catalytic efficiency in this order. The substrates were successfully used to measure the esterolytic activity of white blood cell (WBC) suspension down to 20 WBC $\mu L^{-1}$. They signal the advent of high-resolution quantitative electrochemical LE assays as a proxy for the presence of active leukocytes in the diagnosis of infections.

A. Results

A new class of substrates is described herein, which enable electrochemical LE assays that overcome the limits of optical assays and open the prospect of point-of-care devices for the rapid quantification of infection. In particular, the inventors describe the synthesis of hydrophilic redox substrates for LE, their enzymatic kinetics, and their performance in the development of electrochemical LE assays.

Substrates are based on pyridine compounds that upon reaction with LE release a redox active fragment, which then is oxidized at an electrode yielding a current in a direct proportion to the enzymatic activity of LE. While designing such esters the inventors took into account known structural requirements for LE substrates including the presence of amino acids (e.g., alanine) and sulfonyl groups (Johnson and Schaeper, *Bioconjugate Chem.* 1997, 8:76-80; Bieth, *Elastin and Elastases*, CRC Press Inc., Boca Raton, 1989, vol. II, pp. 23-31; Schechter and Berger, *Biochem. Biophys. Res. Commun.* 1967, 27:157-62; Jackson et al., *Arch. Biochem. Biophys.* 1995, 323:108-14). The synthesis of such esters was accomplished by converting a redox active 1,4-hydroquinone (HQ) into species with a generic formula $R_1$-HQ-$R_1$ (Scheme 1). The substituents $R_1$ were tuned to increase the solubility of $R_1$-HQ-$R_1$ compounds in water, which is essential for their intended use in the electrochemical LE strips where desiccated chemicals must dissolve quickly in aqueous media.

To balance the desired hydrophilicity with the necessary binding and interaction of new compounds with LE, their design incorporated structural changes in a substituent $R_6$. The substrate design focused on increasing compounds' topological polar surface area (tPSA) and decreasing their lipophilicity as assessed by the octanol/water partition coefficient (Log P). This was accomplished by introducing a heterocycle pyridine ring with or without additional polar groups as $R_6$. Following these guidelines, the three compounds I-III were synthesized in one step from the precursor diamine HCl salt 1, the synthesis of which was reported previously (Hanson et al., *Anal. Chem.* 2017, 89:7781-87). Briefly, reacting the HQ with (tert-butoxycarbonyl)-L-alanine in the presence of N-(3-dimethylaminopropyl)-N-ethylcarbodiimide hydrochloride (EDCI) and trimethylamine (TEA) yielded the bis-ester, which was then deprotected under acidic conditions to provide the precursor diamine HCl salt 1. Treatment of diamine 1 with the desired aryl sulfonyl chloride ($R_6$—$SO_2Cl$) and TEA provided the anticipated bis-sulfonamide derivatives I-III (Scheme 2) in low to moderate yields.

Scheme 1. The generic structure of $R_1$-HQ-$R_1$ redox substrates for LE.

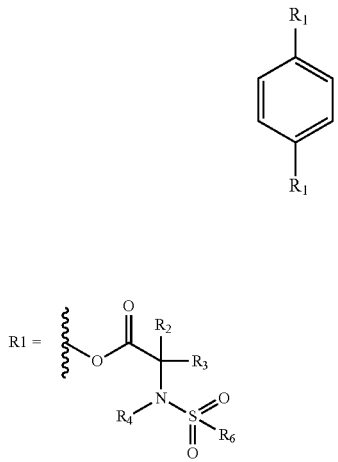

Scheme 2. The one-step synthesis of compounds I-III from the precursor 1.

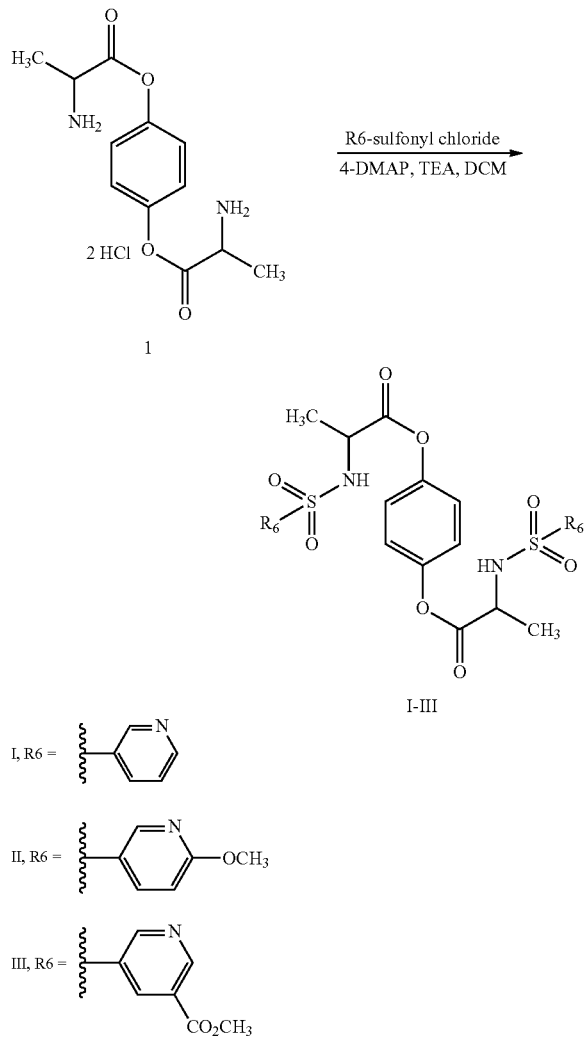

The initial electrochemical tests were performed to assess a degree of the recognition of compounds I-III by LE as its substrates. This was done by using the internally calibrated electrochemical continuous enzyme assay (ICECEA) (Hanson et al., Anal. Chem. 2017, 89:7781-87; Zhang et al., Anal. Chem. 2013, 85:6026-32; Zhang et al., Anal. Chem. 2014, 86:9330-34) to monitor the release of HQ ($C_6H_6O_2$) in a reaction (reaction 1)

  (1)

which was conducted in an electrolytic cell with a glassy carbon (GC) working electrode held at a potential of 0.40 V that was sufficient for the electrooxidation of $C_6H_6O_2$

  (2)

The ICECEA was conducted by using phosphate buffer saline (PBS) solutions (pH 7.40, 154 mM NaCl) that contained either a tested compound, HQ, or LE. The current flowing through the GC electrode was measured while spiking 5.00 mL of a stirred assay solution of tested compound with triplicate aliquots of HQ solution and an aliquot of LE solution (FIG. 1).

FIG. 1B shows that the addition of original HQ to an assay solution at 50, 100, and 150 s yielded extra current in the form of I-t steps. This corroborated that HQ was indeed electro-oxidized at a GC electrode (reaction 2) under such conditions. The addition of LE to a solution at 200 s triggered a rising I-t segment for all three compounds (traces a-c). The rising current can be ascribed to the electro-oxidation of HQ that was steadily released from the compounds in the presence of LE in a solution (reaction 1). The control experiments showed no rising current when LE was added to a solution containing no tested compounds. Thus, the presence of rising I-t segments in the ICECEA traces shown in FIG. 1 is proof that LE recognized compounds I-III as its substrates.

The control experiments with precursor 1 showed no rising I-t segment in the presence of LE in a solution (FIG. 1) indicating the lack of reaction between these two species. In contrast to compounds I-III, the precursor 1 is lacking a structural sulfonamide-carbon ring motif (Scheme 2), which is needed for recognition by LE.

The properties of compounds I-III as LE substrates were further investigated by determining their kinetics of reaction with LE (reaction 1). The initial rate of reaction 1 was measured by ICECEA at a constant LE concentration ($c_{LE}$=6.0 nM; MW=29 kDa) and under the condition of $c_{LE} \ll c_{compound\ I-III}$ ($c_{compound\ I-III}$=1-40 μM). The assays were conducted within a linear range of calibration plot for HQ at a GC electrode. One unit (U) of LE activity was defined as the amount of enzyme that catalyzed the hydrolysis of 1.0 μmole of a compound I-III per minute in a PBS solution at room temperature (21° C.). The LE activity (U $L^{-1}$) was calculated from the equation $$UL^{-1}(\mu M\ min^{-1}) = \frac{AS(\mu A\ s^{-1}) * 60(s\ min^{-1})}{CS\ (\mu A\ \mu M^{-1})} \quad (3)$$

where AS is an assay slope equal to the slope of rising I-t segment and CS is a calibration slope calculated from the I-t steps of ICECEA traces similar to those shown in FIG. 1. FIG. 2 shows that the LE activity ($UL^{-1}$) was proportional to the concentration of compound I-III up to 15-20 μM and plateaued afterwards. The analysis of such plots using the Michaelis-Menten kinetics yielded the Michaelis constants $K_m$ and turnover numbers $k_{cat}$, which are shown in Table 1.

Table 2 reveals two key points about the compounds I-III as LE substrates. First, the small values of $K_m$ indicate their high binding affinity for LE. The available data for optical LE substrates (e.g. $K_m$=0.9-1.5 mM) (Murthy and Karmen, Biochem. Med. Metabol. Bio., 1988, 40:260-68) suggest that the affinity of new LE substrates ($K_m$=8-10 μM) is better by as much as two orders of magnitude. Second, the compound III displays the largest specificity constant $k_{cat}/K_m$ indicating that it has the highest catalytic efficiency in reaction with LE. Table 1 also shows that the compound III has the highest topological surface area (tPSA) and lowest lipophilicity (Log P), which correlate with its highest solubility in water. Compound III has the highest content of oxygen atoms in a substituent $R_6$ among the three compounds. The exact reason for such patterns is not clear at present but these observations may point toward a favorable mechanistic role of hydrogen bonding in the interactions between the compound III and LE.

TABLE 2

| Compound | $K_m$ (μM) | $k_{cat}$ (s$^{-1}$) | $k_{cat}K_m^{-1}$ (M$^{-1}$ s$^{-1}$) | LogP | tPSA (Å$^2$) | Solubility (mg mL$^{-1}$) | Average activity of single WBC (nU) |
|---|---|---|---|---|---|---|---|
| I | 12 | 3.2 | $2.7 \times 10^5$ | 0.69 | 170 | 0.05 | 0.8 |
| II | 14 | 5.3 | $3.8 \times 10^5$ | 1.87 | 188 | 0.50 | 1.5 |
| III | 11 | 6.4 | $5.8 \times 10^5$ | 0.33 | 222 | 4.0 | 4.5 |

Figure 3:
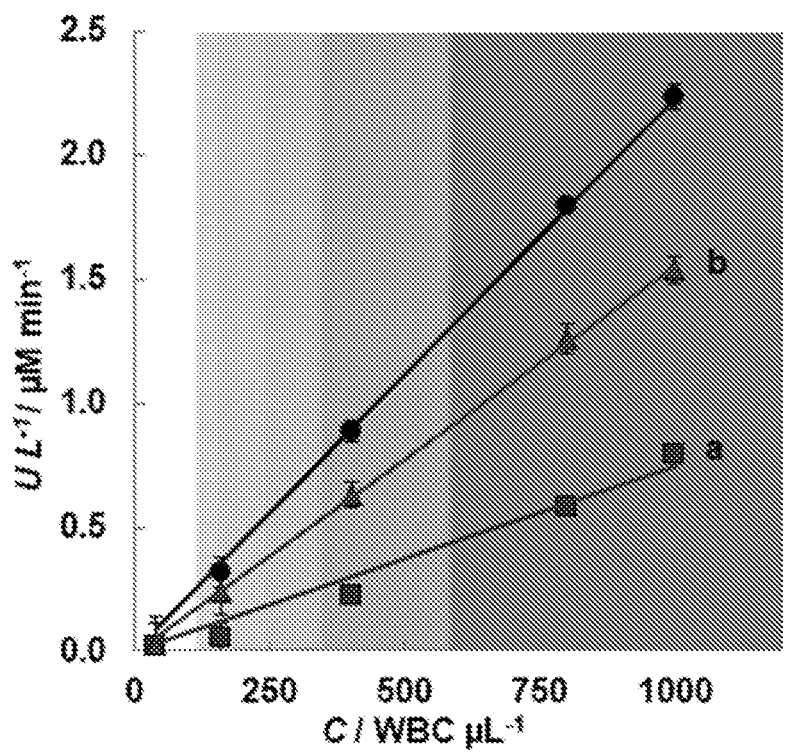
FIG. 3. Dependence of LE activity on the white blood cell (WBC) count in leukocyte suspensions determined by using ICECEA and compound: (a) I, (b) II, and (c) III. Assay solution, 100 µM substrate I, II, or III in a pH 7.40 PBS solution. Concentration of HQ calibration spikes, 0.54 µM. Dilution factor, 100×. Potential, 0.40 V.

Finally, the compounds I-III were tested in the development of electrochemical LE assay using the ICECEA. The assay was optimized with respect to the detection potential, sample dilution factor, and solution composition (pH, concentration). Such assay was used to determine the esterolytic activity of a series of human leukocyte suspensions. FIG. 3 shows that the ICECEA signal (U L$^{-1}$) grew linearly (R$^2$, 0.999-0.992) with the white blood cell (WBC) count in a suspension. As expected, the highest specificity constant $k_{cat}/K_m$ of compound III resulted in the highest assay sensitivity (a slope) and the lowest detection limit down to 20 WBC μL$^{-1}$ (a typical human range is 3,500-10,500 WBC μL$^{-1}$). Accordingly, the average esterolytic activity of single WBC calculated using the slopes of plots in FIG. 3 was the highest when determined using a compound III (Table 2).

FIG. 3 also shows that the ICECEA signal correlated well with the changes in the color intensity of commercial LE test strips. The higher the signal, the more intense was the color of a strip. However, the benefit of electrochemical LE assay is that it provides a numerical output with high resolution allowing to discern differences in LE activities even within the same color zone.

The developed assay is rapid (<5 min), precise (<±5%), and easy to calibrate without any need for LE standard solutions. The unique shape of I-t trace helps avoiding interferences from other redox active species as long as their concentration does not change during the assay.

In summary, the $R_1$-HQ-$R_1$ compounds act as active redox substrates for enzyme leukocyte esterase (LE) when the substituents $R_1$ contain an amino acid, sulfonamide, and heterocycle with or without the polar groups. The $R_6$ substituents can be tuned to enhance the hydrophilicity of such compounds without negatively impacting their recognition by LE. These advances pave the way for developing electrochemical LE strips for measuring infections similar to the electrochemical glucose strips widely used in diabetes monitoring.

B. Materials and Methods

Reagents and Solutions. Chemicals were purchased from established commercial suppliers, including Sigma Aldrich (St. Louis, Mo.), Acros Organics (Pittsburgh, Pa.), Combi-Blocks (San Diego, Calif.), AK Scientific (Union City, Calif.), Fisher Scientific (Hampton, N.H.), and Enamine (Kyiv, Ukraine). Hydroquinone was obtained from Sigma Aldrich. Boc-Ala-OH, pyridine-3-sulfonyl chloride, and 6-methoxypyridine-3-sulfonyl chloride were obtained from Combi-Blocks. 4-Toluenesulfonyl chloride was obtained from Sigma Aldrich, and methyl 5-(chlorosulfonyl)pyridine-3-carboxylate was obtained from Enamine. The $NaH_2PO_4.H_2O$, $Na_2HPO_4$, dimethylsulfoxide (DMSO), trimethylamine (99%, 157008), $Na_2CO_3$, $CH_3COOH$, HCl, and NaOH were from Fisher.

The milky white suspension of human white blood cells in 154 mM NaCl solution was purchased from MyBioSource (cat. #MBS173116, 0.0867 mg mL$^{-1}$ LE protein, $4 \times 10^8$ WBC mL$^{-1}$). The commercial test strips for leukocyte esterase (Siemens Multistix 10 SG) were purchased locally.

The 6.0 mg mL$^{-1}$ stock solutions of compounds I-III were prepared in DMSO. Such solutions were stable for at least several weeks when stored either refrigerated or at room temperature. The 50-mM pH 7.40 phosphate buffer saline (PBS) solution containing 154 mM NaCl was used as a background electrolyte in all electrochemical measurements. All aqueous solutions were prepared using 18-MΩ-cm deionized water that was purified with a Synergy Millipore cartridge system.

Preparation of Leukocyte Suspensions. The original suspension of leukocytes was diluted 10 times with a PBS solution that contained 10 vol. % DMSO and left for 30 min on a shaker table at 60 rpm to lyse the leukocytes chemically. Such a suspension preserved a constant esterolytic activity for at least 5 days when stored in a refrigerator at 4° C. It was used as a solution C (vide infra) for the ICECEA.

Electrochemical Measurements. All electrochemical measurements were performed in the three-electrode cell with a 3.0-mm-dia. glassy carbon (GC) working electrode (BAS), Pt wire counter electrode, and Ag/AgCl/3M NaCl (BAS) reference electrode. The voltammograms and amperograms were recorded by using a CHI 601B workstation (CH Instruments, Inc.). The working electrode was wet polished on an Alpha A polishing cloth (Mark V Lab) with successively smaller particles (0.3 and 0.05-μm diameter) of alumina. The slurry that accumulated on the electrode surface was removed by a 30-s sonication in deionized water and methanol. All electrochemical experiments were done at room temperature (21° C.). They were repeated at least three times to report the precision of results with the relative standard deviation.

Solubility. The solubility of compounds I-III was determined by UV-visible spectrophotometry. The compounds were dissolved in water at room temperature (21° C.) to make a series of solutions with increasing concentration. The solutions were stirred continuously and their spectra were recorded until steady-state equilibrium was reached. Below the solubility limit, the steady-state background-corrected absorbance of solution at 270 nm ($A_{270}$) was directly proportional to the compound concentration as expected by the Beer-Lambert law. Above the solubility limit, the absorbance steadily levelled off. The low- and high-concentration regions of plots $A_{270}$ vs. compound concentration were linearized and extrapolated to a crossing point, which was taken as the solubility of compound.

General Synthetic Procedures. Unless otherwise indicated all reactions were conducted in standard commercially available glassware using standard synthetic chemistry methods and setup. All air- and moisture-sensitive reactions were performed under nitrogen atmosphere with dried solvents and glassware under anhydrous conditions. Starting materials and reagents were commercial compounds of the highest purity available and were used without purification. Solvents used for reactions were indicated as of commercial dry or extra-dry or analytical grade. The identity of new compounds was confirmed by $^1$H NMR, HPLC-MS, and HRMS. The purity was ensured to be ≥95%.

NMR. $^1$H NMR experiments were recorded on Agilent DD2 400 MHz spectrometer at ambient temperature. Samples were dissolved and prepared in deuterated solvents (CDCl$_3$, CD$_3$OD and DMSOd$_6$) with residual solvents being used as the internal standard. All deuterated solvent peaks were corrected to the standard chemical shifts (CDCl$_3$, d$_H$=7.26 ppm; CD$_3$OD, d$_H$=3.31 ppm; DMSO-d$_6$, d$_H$=2.50 ppm). Spectra were all manually integrated after automatic baseline correction. Chemical shifts (d) are given in parts per million (ppm), and coupling constants (J) are given in Hertz (Hz). The proton spectra are reported as follows: d (multiplicity, coupling constant J, number of protons). The following abbreviations were used to explain the multiplicities: app=apparent, br=broad, d=doublet, dd=doublet of doublets, ddd=doublet of doublet of doublets, dddd=doublet of doublet of doublet of doublets, dt=doublet of triplets m=multiplet, s=singlet, t=triplet, q=quartet, and p=pentet.

HPLC-MS. All samples were analyzed on Agilent 1290 series HPLC system comprised of binary pumps, degasser, and UV detector equipped with an auto-sampler that was coupled with Agilent 6150 mass spectrometer. Purity was determined via UV detection with a bandwidth of 170 nm in the range from 230-400 nm. The general LC parameters were as follows: Column—Zorbax Eclipse Plus C18, size 2.1×50 mm; Solvent A: 0.10% formic acid in water, Solvent B: 0.00% formic acid in acetonitrile; Flow rate—0.7 mL/min; Gradient: 5% B to 95% B in 5 min and hold at 95% B for 2 min; UV detector—channel 1=254 nm, channel 2=254 nm. Mass detector Agilent Jet Stream—Electron Ionization (AJS-ES).

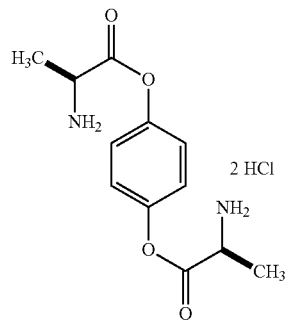

Synthesis of 1,4-phenylene (2S,2'S)-bis(2-aminopropanoate)-bis hydrochloride (Precursor 1): A 4.0 M HCl solution in 1,4-dioxane (60 mL) was slowly added to 1,4-phenylene (2S,2'S)-bis(2-((tert-butoxycarbonyl)amino)propanoate) (1.87 g, 4.4 mmol) at room temperature. The mixture was allowed to stir for 30 minutes at room temperature, after which time the resulting precipitate was filtered, washed with cold diethyl ether, and dried under reduced pressure. The resulting white solid, 1,4-phenylene (2S,2'S)-bis(2-aminopropanoate)-bis hydrochloride (1.31 g, 93% yield) was used without further purification; $^1$H NMR (400 MHz, CD$_3$OD) δ 7.30 (s, 4H), 4.42 (q, J=7.2 Hz, 2H), 1.72 (d, J=7.3 Hz, 6H). MS (m/z) 505.3 (2M+H$^+$), 253.2 (M+H$^+$).

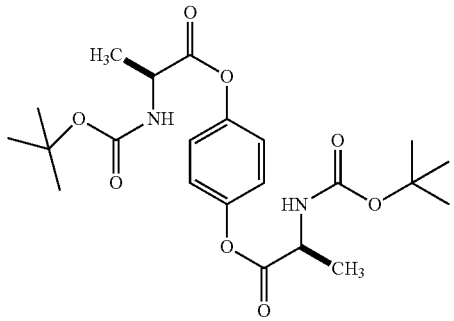 [SMILES: C[C@H](NC(=O)OC(C)(C)C)C(=O)Oc1ccc(OC(=O)[C@H](C)NC(=O)OC(C)(C)C)cc1]

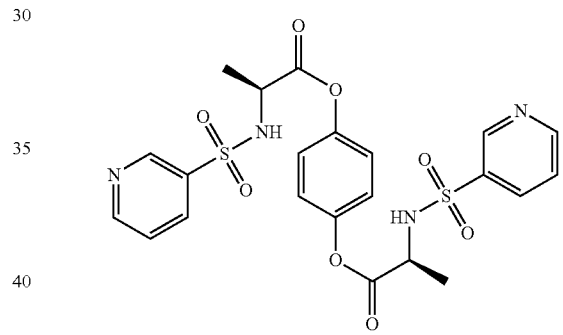

Synthesis of 1,4-phenylene (2S,2'S)-bis(2-((tert-butoxycarbonyl)amino)propanoate): A flame-dried vessel purged with nitrogen was charged with hydroquinone (1.04 g, 9.5 mmol) and acetonitrile (120 mL) at room temperature. To this stirred solution was added (tert-butoxycarbonyl)-L-alanine (3.62 g, 19 mmol) and 4-dimethylaminopyridine (0.117 g, 0.96 mmol). The mixture was allowed to stir for 5 minutes before adding N-(3-dimethylaminopropyl)-N'-ethylcarbodiimide hydrochloride (3.9 g, 20 mmol), followed by triethylamine (2.8 mL, 20 mmol). The reaction mixture was stirred at room temperature for 12 hours. The mixture was poured into ice-cold 1.0 M HCl (300 mL) and allowed to stir for 30 minutes. The resulting precipitate was filtered and dried under reduced pressure. The crude solid was recrystallized in a mixture of hexanes and ethyl acetate (4:1). The solid was filtered and dried under reduced pressure to yield 2.57 g (64% yield) of 1,4-phenylene (2S,2'S)-bis(2-((tert-butoxycarbonyl)amino)propanoate) as a white solid; $^1$H NMR (400 MHz, CDCl$_3$) δ 7.12 (s, 4H), 5.07 (br s, 2H), 4.52 (br m, 2H), 1.51 (d, J=7.7 Hz, 6H), 1.47 (s, 18H).

Synthesis of 4-(((pyridin-3-ylsulfonyl)-L-alanyl)oxy)phenyl (pyridin-3-ylsulfonyl)-L-alaninate (Compound I): To a stirred solution of 1,4-phenylene (2S,2'S)-bis(2-aminopropanoate)-bis hydrochloride (0.282 g, 0.87 mmol) in anhydrous dichloromethane (5.0 mL) under nitrogen atmosphere was added pyridine-3-sulfonyl chloride (0.380 g, 2.1 mmol), 4-dimethylaminopyridine (0.011 g, 0.07 mmol), and triethylamine (0.40 mL, 2.9 mmol). The mixture was allowed to stir at room temperature overnight. The crude reaction mixture was treated with equal portions (~5 mL) of water and ethyl acetate and transferred to a separatory funnel. The layers were separated and the aqueous layer was extracted with ethyl acetate (3×2 mL). The combined organic layers were washed with brine (~5 mL), dried with anhydrous sodium sulfate, decanted, and concentrated under reduced pressure. The crude product was subjected to column chromatography to yield 4-(((pyridin-3-ylsulfonyl)-L-alanyl)oxy)phenyl (pyridin-3-ylsulfonyl)-L-alaninate (0.191 g, 41% yield) as an off-white solid; $^1$H NMR (400 MHz, DMSO-d$_6$) δ 8.99 (br d, J=2.3 Hz, 2H), 8.83 (s, 2H), 8.81-8.78 (br d, 2H), 8.22 (dt, J=8.1, 2.0 Hz, 2H), 7.63 (dd, J=8.1, 4.8 Hz, 2H), 6.96 (s, 4H), 4.29 (q, J=7.1 Hz, 2H), 1.38 (d, J=7.2 Hz, 6H). $^{13}$C NMR (101 MHz, DMSO-d$_6$) δ 170.90, 153.50, 147.95, 147.39, 137.96, 134.91, 124.68, 122.75, 51.65, 40.86, 18.60. HRMS m/z [M+H]+ calculated for $C_{22}H_{22}N_4O_8S_2$: 535.0952. Found: 535.0959.

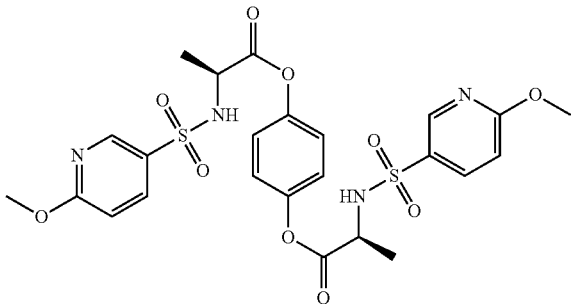

Synthesis of 4-((((6-methoxypyridin-3-yl)sulfonyl)-L-alanyl)oxy)phenyl ((6-methoxypyridin-3-yl)sulfonyl)-L-alaninate (Compound II): To a stirred solution of 1,4-phenylene (2S,2'S)-bis(2-aminopropanoate)-bis hydrochloride (0.286 g, 0.88 mmol) in anhydrous dichloromethane (5.0 mL) nitrogen atmosphere was added 6-methoxypyridine-3-sulfonyl chloride (0.460 g, 2.2 mmol), 4-dimethylaminopyridine (0.011 g, 0.07 mmol), and triethylamine (0.40 mL, 2.9 mmol). The mixture was allowed to stir at room temperature overnight. The crude reaction mixture was treated with equal portions (~5 mL) of water and ethyl acetate and transferred to a separatory funnel. The layers were separated and the aqueous layer was extracted with ethyl acetate (3×2 mL). The combined organic layers were washed with brine (~5 mL), dried with anhydrous sodium sulfate, decanted, and concentrated under reduced pressure. The crude product dissolved in dichloromethane and precipitated out with hexanes. The solid was filtered, washed with hexanes, and dried under reduced pressure to yield 4-((((6-methoxypyridin-3-yl)sulfonyl)-L-alanyl)oxy)phenyl ((6-methoxypyridin-3-yl)sulfonyl)-L-alaninate (0.0782 g, 15% yield) as a white solid; $^1$H NMR (400 MHz, DMSO-d$_6$) δ 8.62 (d, J=8.1 Hz, 2H), 8.60 (d, J=2.5 Hz, 2H), 8.06 (dd, J=8.8, 2.6 Hz, 2H), 7.13-6.86 (m, 6H), 4.21 (p, J=7.3 Hz, 2H), 3.91 (s, 6H), 1.37 (d, J=7.1 Hz, 6H). $^{13}$C NMR (101 MHz, DMSO-d$_6$) δ 171.00, 166.06, 147.98, 146.65, 138.00, 131.14, 122.71, 111.75, 54.50, 51.59, 33.64, 18.58. HRMS m/z [M+H]+ calculated for $C_{24}H_{26}N_4O_{10}S_2$: 595.1163. Found: 595.1178.

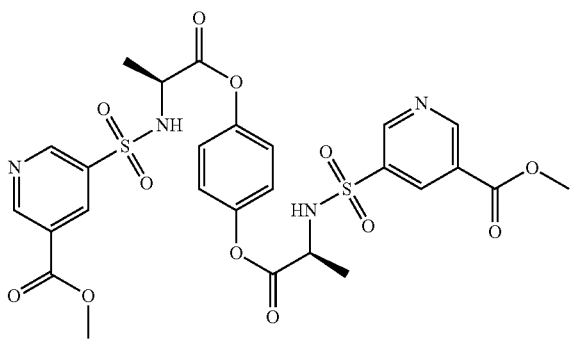 [SMILES: COC(=O)c1cncc(S(=O)(=O)N[C@@H](C)C(=O)Oc2ccc(OC(=O)[C@H](C)NS(=O)(=O)c3cncc(C(=O)OC)c3)cc2)c1]

Synthesis of 4-(((methyl 5-(chlorosulfonyl)pyridine-3-carboxyl)-L-alanyl)oxy)phenyl (methyl 5-(chlorosulfonyl)pyridine-3-carboxy)-L-alaninate (Compound II): To a stirred solution of 1,4-phenylene (2S,2'S)-bis(2-aminopropanoate)-bis hydrochloride (0.277 g, 0.86 mmol) in anhydrous ethyl acetate (4.4 mL) was added trimethylamine before chilling to 0° C. Methyl 5-(chlorosulfonyl)pyridine-3-carboxylate (0.500 g, 2.1 mmol) was added under nitrogen atmosphere followed by warming to room temperature and allowing to stir for 4 h. The crude reaction mixture was treated with equal portions (~5 mL) of water and ethyl acetate and transferred to a separatory funnel. The layers were separated and the aqueous layer was extracted with ethyl acetate (3×2 mL). The combined organic layers were dried with anhydrous sodium sulfate, decanted, and concentrated under reduced pressure. The crude product was subjected to column chromatography to yield 4-(((methyl 5-(chlorosulfonyl)pyridine-3-carboxyl)-L-alanyl)oxy)phenyl (methyl 5-(chlorosulfonyl)pyridine-3-carboxy)-L-alaninate (0.187 g, 34% yield) as a white solid; $^1$H NMR (400 MHz, DMSO-d$_6$) δ 9.18 (dd, J=9.4, 2.1 Hz, 4H), 8.96 (br s, 2H), 8.57 (t, J=2.2 Hz, 2H), 6.90 (s, 4H), 3.99 (q, J=7.1 Hz, 2H), 3.87 (s, 6H), 1.35 (d, J=7.2 Hz, 6H). $^{13}$C NMR (101 MHz, DMSO-d$_6$) δ 170.73, 164.38, 153.33, 150.97, 147.89, 138.14, 135.31, 126.34, 122.65, 53.30, 51.67, 18.62. HRMS m/z [M+H]+ calculated for $C_{26}H_{26}N_4O_{12}S_2$: 651.1061. Found: 651.1073.

The invention claimed is:
1. A hydrophilic redox leukocyte esterase substrate having a chemical formula of Formula I or a pharmaceutically acceptable salt thereof:

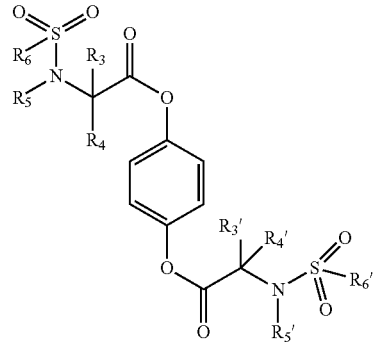

Formula I wherein,
$R_3$, $R_3'$, $R_4$, and $R_4'$ are independently hydrogen, $C_1$ to $C_8$ alkyl, $C_3$ to $C_7$ cycloalkyl, or substituted $C_3$ to $C_7$ cycloalkyl;

$R_5$ and $R_5'$ are independently hydrogen, saturated $C_1$-$C_6$ alkyl, mono-unsaturated $C_1$-$C_6$ alkyl, poly-unsaturated $C_1$-$C_6$ alkyl, $C_3$ to $C_7$ cycloalkyl, or substituted $C_3$ to $C_7$ cycloalkyl; and $R_6$ and $R_6'$ are pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, azaindolyl, aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, or 1,4-dioxaspiro[4.2]heptyl.

2. The substrate of claim 1, wherein the substrate is 4-{[(2S)-2-(4-methylbenzenesulfonamido)propanoyl]oxy}phenyl(2S)-2-(4-methylbenzenesulfonamido)propanoate; 4-{[(2S)-2-(pyridine-3-sulfonamido)propanoyl]oxy}phenyl (2S)-2-(pyridine-3-sulfonamido)propanoate; 4-{[(2S)-2-(6-methoxypyridine-3-sulfonamido)propanoyl]oxy}phenyl (2S)-2-(6-methoxypyridine-3-sulfonamido)propanoate; or methyl 5-{[(2S)-1-(4-{[(2S)-2-[5-(methoxycarbonyl)pyridine-3-sulfonamido]propanoyl]oxy} phenoxy)-1-oxopropan-2-yl] sulfamoyl} pyridine-3-carboxylate.

3. A method for detecting leukocyte esterase (LE) activity comprising contacting a sample with a substrate of claim 1 forming a test sample and detecting cleavage of the substrate by LE in the test sample.

4. The method of claim 3, wherein detecting cleavage of the substrate by LE in the test sample is by electrochemical detection.

5. The method of claim 4, wherein electrochemical detection is by a glassy carbon electrode system.

6. The method of claim 3, wherein the substrate concentration in the test sample is between 10 and 2000 mg/L.

7. A reaction medium comprising a substrate of claim 1 in contact with an electrode.

8. The reaction medium of claim 7, wherein the electrode is a carbon electrode.

9. The reaction medium of claim 7, wherein the electrode is a glassy carbon electrode.

10. The reaction medium of claim 7, wherein the electrode is a noble metal electrode.

* * * * *